US00PP19859P2

(12) United States Plant Patent
Shiotsuki

(10) Patent No.: US PP19,859 P2
(45) Date of Patent: Mar. 24, 2009

(54) *NEMESIA* PLANT NAMED 'NAKNEM002'

(50) Latin Name: *Nemesia caerulea*
Varietal Denomination: Naknem002

(75) Inventor: Shouji Shiotsuki, Ashigara Kami-gun (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 12/074,773

(22) Filed: Mar. 6, 2008

(51) Int. Cl.
*A01H 5/00* (2006.01)

(52) U.S. Cl. ..... Plt./458

(58) Field of Classification Search ..... Plt./458
See application file for complete search history.

*Primary Examiner*—Kent L Bell
(74) *Attorney, Agent, or Firm*—Jondle & Associates, P.C.

(57) ABSTRACT

A new *Nemesia* plant particularly distinguished by its compact plant growth habit, branching, flowering at the top of the plant and blue flower color is disclosed.

1 Drawing Sheet

Genus and species: *Nemesia caerulea.*
Variety denomination: 'NAKNEM002'.

BACKGROUND OF THE NEW PLANT

The present invention comprises a new and distinct cultivar of *Nemesia,* botanically known as *Nemesia caerulea,* and hereinafter referred to by the cultivar name 'NAKNEM002'. The new cultivar originated from a hybridization made in 2003 in Fujisawa, Japan. An initial cross was made between a patented *Nemesia caerulea* (*N. foetens*) plant 'Hubbird' (U.S. Plant Pat. No. 12,014) and an individual unnamed, unpatented proprietary *Nemesia caerulea* plant, both having a blue flower color.

In spring 2003, the female parent line 'Hubbird' and the proprietary male parent were crossed and the $F_1$ plant line was created. The $F_1$ seeds produced by the hybridization were sown in a greenhouse and later transplanted to an outdoor trial. The $F_1$ plants were evaluated and selected based on flower color, plant growth habit, flowering at the top of the plant and stem strength.

The $F_2$ generation seed was sown in October 2003, and the $F_3$ generation seed was sown in September 2004 and later transplanted to an outdoor trial. In December 2004, 10 plants were selected for further evaluation and for asexual propagation. In March 2005, a single plant selection, 'BB-2A-7', was chosen based on its blue flower color, compact and branching plant growth habit, flowering at the top of the plant and strong stem. This selection was asexually propagated by cuttings in Fujisawa, Japan and further evaluated in Fujisawa, Japan in 2005 in an indoor pot trial and an outdoor trial to confirm the uniformity and stability of its characteristics. The selection was found to reproduce true to type in successive generations of asexual propagation and subsequently was named 'NAKNEM002'.

The new cultivar was created in 2003 in Fujisawa, Japan and has been asexually reproduced repeatedly in Fujisawa, Japan over a four-year period. The plant has also been trialed in Salinas, Calif. The present invention has been found to retain its distinctive characteristics through successive asexual propagations.

SUMMARY OF THE INVENTION

The following are the most outstanding and distinguishing characteristics of this new cultivar when grown under normal horticultural practices in Salinas, Calif. and Fujisawa, Japan:

1. Blue flowers;
2. Compact growth habit;
3. Branching; and
4. Flowering at the top of the plant.

DESCRIPTION OF THE PHOTOGRAPHS

This new *Nemesia* plant is illustrated by the accompanying photographs which show blooms, buds, and foliage of the plant in full color; the colors shown are as true as can be reasonably obtained by conventional photographic procedures. The photographs are of a 4-month-old plant grown in a greenhouse with natural light in a spring trial setting.

DESCRIPTION OF THE NEW CULTIVAR

Figure 1:
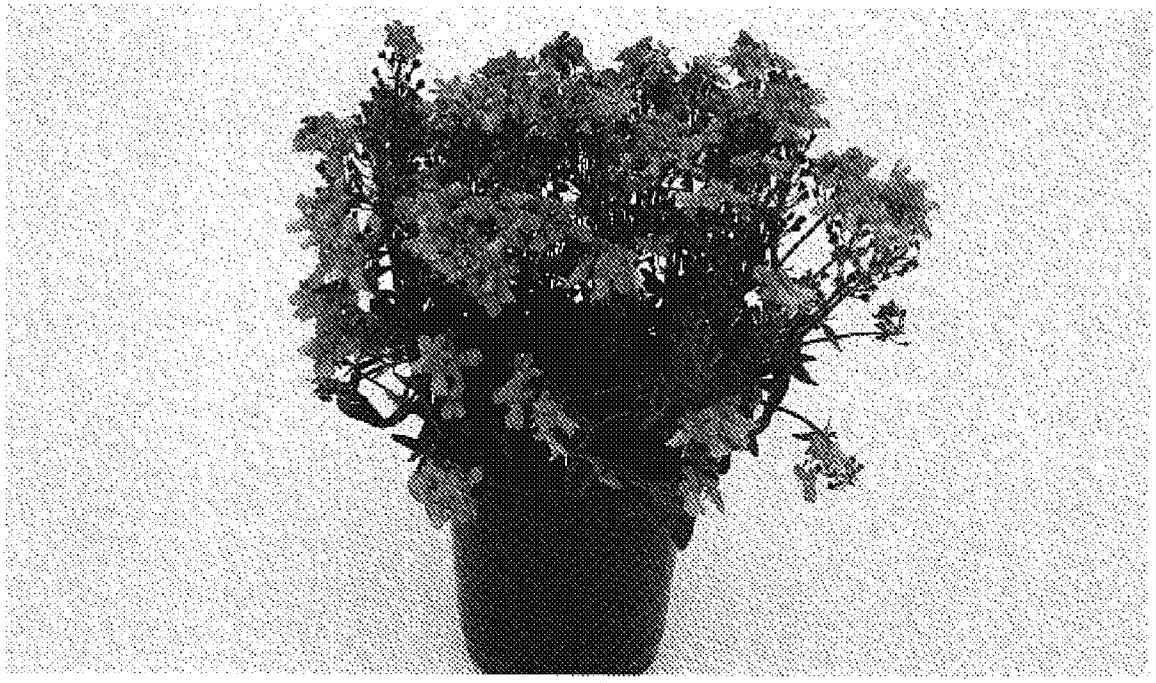
FIG. 1 shows overall plant habit including blooms, buds, and mature foliage.
Figure 2:
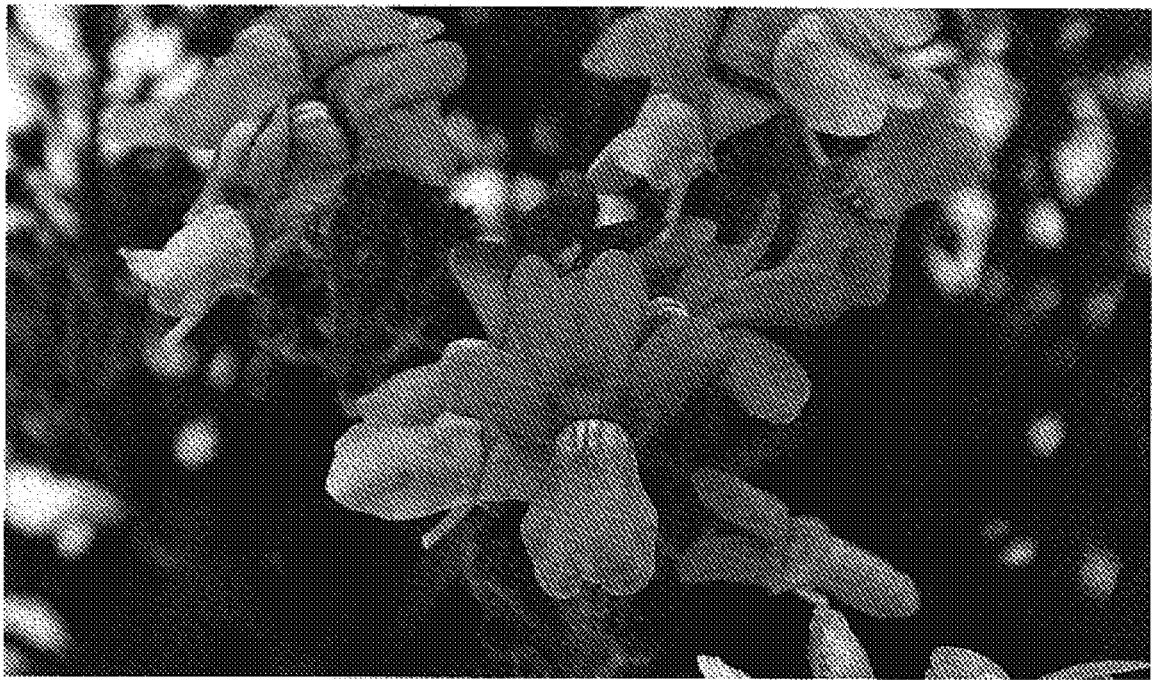
FIG. 2 shows a close-up of a mature flower.

The following detailed descriptions set forth the distinctive characteristics of 'NAKNEM002'. The data which define these characteristics were collected from asexual reproductions carried out in Salinas, Calif. The plant history was taken on four-month-old plants grown from transplant in 5-inch pots from rooted cuttings under greenhouse conditions. The plants were pinched by nipping and shearing off new growth to force branching and increased numbers of blooms later. Color readings were taken under natural light. Color references are primarily to the RHS Colour Chart of The Royal Horticultural Society of London (R.H.S.) (2001 edition). Anatomic labels are from *The Cambridge Illustrated Glossary of Botanical Terms,* by M. Hickey and C. King, Cambridge University Press.

DESCRIPTION OF THE NEW PLANT

Classification:

*Family.*—Scrophulariaceae

*Botanical name.*—*Nemesia caerulea* (also known as *N. foetens* and *N. fruticans*).

*Common names.*—*Nemesia,* Wildeleeubekkie.

Parentage:

*Female parent.*—A blue-flowered individual plant of *Nemesia caerulea* 'Hubbird' (U.S. Plant Pat. No. 12,014).

*Male parent.*—A blue-flowered unnamed individual plant of a proprietary line of *Nemesia caerulea* (Unpatented).

Growth:

*Time to produce a rooted cutting.*—Cuttings will colonize a 2.5 cm diameter by 2.5 cm tall greenhouse tray cell with peat-based plant media in approximately three to four weeks. Cuttings are dipped in a normal dilution (1:9) of DIP 'N GROW root inducing solution in water. The trays are misted hourly during rooting.

*Environmental conditions for plant growth.*—Rooted cuttings are transplanted to pots with a 16 cm diameter, two plants per pot. Peat-based growing media is used. The pots are watered using a 150 to 200 ppm fertilizer solution using 20-10-20 fertilizer. The soil is allowed to dry between watering. During the first few weeks after transplanting the plants should have evening temperatures around 13° C. to 16° C. for good root growth. When plants reach 7.5 to 10 cm in height they are pinched back to 5 to 6 leaves to promote branching. Spring and summer daytime high temperatures in Salinas, Calif., where the data was collected, range from 16° C. to 25° C.

*Time to bloom from propagation.*—Approximately four weeks when rooted vegetative cuttings are transferred to a 5-inch diameter pot. Flowering season is all year in the United States. Vernalization is not required to induce flowering.

General plant description:

*Habit.*—Branching, very compact plant growth habit, fairly vigorous.

*Height.*—18.0 cm from soil line to top of plant, 1.0 cm from soil line to first node.

*Spread.*—4.0 cm to 25.0 cm.

*Life cycle.*—Annual, spring plant.

*Time to produce a rooted cutting.*—3 to 4 weeks.

*Time to bloom from propagation.*—4 to 6 weeks.

*Flowering season.*—Spring to Fall.

*Root system description.*—Fine and fibrous.

*Rooting habit.*—Branching.

*Temperature tolerances.*—Approximately 10° C. to 35° C.

Branches:

*Branching.*—Freely branching

*Number of branches.*—6 primary branches and numerous secondary and tertiary lateral branches.

*Length of branches.*—1.5 cm from soil line to first node, 4.0 cm between the nodes, 18.0 cm total length.

*Diameter of branches.*—0.4 cm width by 0.1 cm depth.

*Internode length.*—4.0 cm.

*Strength of branches.*—Moderately strong.

*Shape of all branches in cross section.*—Rectangular with edges or longitudinal ridges on 4 sides.

*Branch color.*—RHS 143B (Green).

*Branch texture.*—Smooth, glabrous.

*Anthocyanin.*—None.

*Branch pubescence.*—None.

Leaves:

*Arrangement.*—Opposite, simple.

*Shape.*—Lanceolate.

*Tip.*—Acute.

*Base.*—Attenuate.

*Margin.*—Dentate (toothed).

*Length.*—4.0 cm.

*Width.*—1.5 cm.

*Color.*—Upper: RHS 137A (Green). Lower: RHS 137C (Green).

*Attachment.*—Decurrant.

*Variegation.*—None.

*Fragrance.*—Absent.

*Texture* (*both surfaces*).—Dull, glabrous.

*Pubescence.*—None.

*Venation.*—Pinnate.

*Vein color.*—Upper: RHS 137A (Green). Lower: RHS 138B (Green).

Flower bud:

*Quantity per inflorescence.*—12 to 14 total, 3 to 6 open at any one time.

*Shape.*—Ovoid with nectar spur.

*Texture.*—Slight amount of pubescence; pubescence color is RHS N155A (White).

*Size.*—Length: 0.7 cm (including nectar spur). Diameter: 0.4 cm.

*Color.*—RHS 79D (Purple).

Inflorescence:

*Inflorescence type, arrangement.*—Zygomorphic solitary flowers arranged on terminal racemes; 5 petals in a single whorl. Flowers acropetally from base to apex. Flowers bilabiate with nectar spur. Flowers face upright and outward.

*Lastingness of flowers on the plant.*—About 6 to 8 weeks.

*Number of flowers per inflorescence.*—Approximately 4.

*Inflorescence length.*—4.0 cm.

*Inflorescence diameter.*—2.5 cm.

*Flower diameter.*—1.0 cm.

*Flower depth including nectar spur.*—1.5 cm.

*Nectar spur length.*—0.4 cm.

*Fragrance.*—Sweet floral scent similar to honeysuckle, snapdragon or stock.

*Self-cleaning or persistent.*—Not persistant.

Petals:

*Quantity* (*per flower*).—5.

*Size.*—Length (both upper and lower lips): 1.0 cm. Width (both upper and lower lips): 2.0 cm.

*Arrangement/shape.*—5 petals in a single whorl. Bilabiate with nectar spur. Upper lip has 4 lobes connected at center of petal. Lower lip has single lobe curled outward at the top with nectar spur at bottom. Lower petal has a white center which guides pollinators.

*Apex.*—Retuse.

*Margin.*—Entire.

*Color* (*mature*).—Upper lip: RHS 92A (Violet-Blue). Lower lip: RHS 92B (Violet-Blue) with RHS N155A (White) at center.

*Texture* (*both upper and lower lips*).—Glabrous, soft and smooth.

*Nector spur color.*—RHS 92D (Violet-Blue).

*Nectar guide color.*—RHS N155A (White).

*Spur length.*—0.4 cm.
*Spur diameter at base.*—0.2 cm.
*Spur diameter at tip.*—0.1 cm.
*Spur texture.*—Glabrous, soft and smooth.

Calyx:
*Calyx shape.*—Star-shaped.
*Sepals.*—Quantity: 5 sepals, fused at base. Shape: Lanceolate. Apex: Acute. Base: Fused. Margin: Entire. Color: RHS 143B (Green). Length: 0.3 cm. Diameter: 0.1 cm. Texture (both surfaces): Slight amount of pubescence.

Pedicel:
*Length.*—0.8 cm.
*Diameter.*—0.05 cm.
*Color.*—RHS 143B (Green).
*Texture.*—Moderate amount of pubescence; pubescence color RHS N155A (White).

Peduncle:
*Length.*—10.0 cm (to first node).
*Diameter.*—0.2 cm.
*Color.*—RHS 143B (Green).
*Texture.*—Smooth, glabrous.

Reproductive organs:
*Stamens.— Number per flower:* 4. Length: 0.25 cm. Filament color: RHS N155A (White). Filament length: 0.2 cm. Filament diameter: 0.05 cm. Anther color: RHS 9A (Yellow). Anther length: Less than 0.1 cm. Pollen amount: Scarce, small amount. Pollen color: RHS 9B (Yellow).
*Pistil.*—Pistil number: 1. Pistil length: 0.15 cm. Stigma color: RHS 143C (Green). Stigma length: Less than 0.1 cm. Style length: 0.1 cm. Style color: RHS 143D (Green). Ovary: Inferior.

Fruit and Seed Set: None.
Disease and Insect Resistance: Has not been observed.

COMPARISON WITH PARENTAL AND COMMERCIAL CULTIVARS

'NAKNEM002' is a new and unique variety of *Nemesia* owing to its compact plant growth habit, branching, flowering at the top of the plant, and blue flower color. 'NAKNEM00' is most similar to the female parent *Nemesia* variety 'Hubbird' (U.S. Plant Pat No. 12,014); however, there are differences between the two varieties as shown in Table 1.

TABLE 1

| Characteristic | 'NAKNEM002' | 'Hubbird' |
|---|---|---|
| Petal color: Upper lip | RHS 92A (Violet-Blue) | RHS 86B to 88C to 88D to 87B |
| Nectar guide color | RHS N155A (White) | RHS 1B to 1C (Yellow-green) |
| Flower bud color | RHS 79D (Purple) | RHS 76D (Purple) |
| Pedicel color | RHS 143B (Green) | RHS 138A (Green) |

'NAKNEM002' is similar to its parents however there are differences as shown in Table 2.

TABLE 2

| Characteristic | 'NAKNEM002' | Male Parent (Unnamed) | Female Parent 'Hubbird' |
|---|---|---|---|
| Flower color | Clear Blue | Clear Blue | Blue |
| Plant growth habit | Compact, branching | Compact, branching | Upright, tall, less branching |
| Blooming | Multi-flowering and upfacing | Multi-flowering and upfacing. Flowers initiate from a very low node position | Slightly upfacing |

I claim:

1. A new and distinct cultivar of *Nemesia* plant as shown and described herein.

* * * * *